United States Patent
Ishler

(10) Patent No.: US 6,949,070 B2
(45) Date of Patent: Sep. 27, 2005

(54) NON-INVASIVE BLOOD GLUCOSE MONITORING SYSTEM

(76) Inventor: Larry W. Ishler, 4258 W. 28th St., Erie, PA (US) 16506

(*) Notice: Subject to any disclaimer, the term of this patent is extended or adjusted under 35 U.S.C. 154(b) by 148 days.

(21) Appl. No.: 10/646,881

(22) Filed: Aug. 21, 2003

(65) Prior Publication Data

US 2005/0043603 A1    Feb. 24, 2005

(51) Int. Cl.$^7$ .............................................. A61B 5/00
(52) U.S. Cl. ...................................... 600/365; 600/549
(58) Field of Search .............................. 600/345–350, 600/365, 549

(56) References Cited

U.S. PATENT DOCUMENTS 5,601,079 A * 2/1997 Wong et al. ................ 600/322

2003/0023151 A1 * 1/2003 Khalil et al. ................ 600/309
2004/0265941 A1 * 12/2004 Galen et al. .................. 435/14

* cited by examiner

Primary Examiner—Robert L. Nasser

(57) ABSTRACT

A non-invasive blood glucose monitoring system wherein sensors in contact with separate locations on the ear and calibrated to be accurate to at least ±0.035 degrees Centigrade take the ear temperatures at these locations up to four times per minute continuously to calculate the temperature differential, and using this temperature differential in conjunction with a value determined by taking the square root of the product of the fasting blood glucose and HbA1c that becomes the base line glucose reference level, it can be determined that if the temperature differential decreases, then the blood glucose has increased 1 mg/dl per approximately 0.024 C, while if the temperature differential increases, the blood glucose has decreased 1 mg/dl per approximately 0.024 C.

11 Claims, 2 Drawing Sheets

NON-INVASIVE BLOOD GLUCOSE MONITORING SYSTEM

FIELD OF THE INVENTION

The present invention pertains to self-administered analyte monitoring systems for diabetics, and, more particularly pertains to a non-invasive blood glucose monitoring system that provides real-time analysis of blood glucose levels to help type 1 and type 2 diabetics manage their blood glucose level.

SUMMARY OF THE INVENTION

According to current estimates approximately 100 million people throughout the world, including 17 million Americans, are afflicted with diabetes mellitus. Over the next ten years these numbers are expected to double. Diabetes is the result of the body's inability to metabolize glucose through the production of insulin by the pancreas. Through the work of Dr. Frederick Banting and Charles Best in the 1920's, it was discovered that insulin synthesized from non-human sources could be used by diabetics to control blood glucose levels so that diabetics could maintain some normality of living.

To maintain a normal lifestyle, the diabetic must carefully and continuously monitor his or her blood glucose level on a daily and even hourly basis. For example, blood glucose levels are critical in the maintenance and determination of cognitive functioning. With respect to the brain, blood glucose levels with respect to the brain influence and affect memory, awareness, and attention; thus, the consequences of reduced or elevated blood glucose levels on cognitive function are more drastic for anyone with poor glucose control such as individuals afflicted with diabetes. If blood glucose is too high a condition of hyperglycemia (high blood sugar) results and one is in danger of falling into a coma; if blood glucose is too low the condition of hypoglycemia (low blood sugar) results and one is in danger of losing consciousness. As a result of years of scientific research, science has uncovered the interrelationships among a person's body weight, lifestyle, food intake, diet and exercise as critical factors in attaining a successful insulin therapy.

Foremost in the management of diabetes and the attainment of a successful insulin therapy is the need to continuously monitor one's blood glucose level. Historically this has been accomplished through painful, repetitive blood glucose tests requiring finger pricks three to four times daily. The primary reason for this regimen is that blood glucose levels fluctuate and stay out of balance until the next test or injection, and such fluctuations and imbalances greatly increase the risk of tissue and organ damage. However, the pain and inconvenience of the finger prick testing tend to discourage diabetics from adhering to the testing regimen as closely as they should. Thus, both the prior art and prior research disclose a number of techniques and systems for monitoring blood glucose levels in a less invasive manner.

For example, Phillips et al. (U.S. Pat. No. 5,968,760) discloses a method for determining an analyte method in a fluid by taking a reflectance reading from a surface of an inert porous matrix and then applying the fluid to be analyzed to another surface so that two reflectance measurements at two separate wavelengths can be made with the method and apparatus suitable for measuring blood glucose levels without separation of red blood cells from serum or plasma.

The Braig patent (U.S. Pat. No. 6,580,934) discloses a method and apparatus for detecting concentrations of a substance in a body by inducing a time-varying temperature on a surface of a body, varying the temperature by surface temperature variation, and then determining substance concentration based on the absorbance from radiation emitted from the surface of the body.

The Steffes patent (U.S. Pat. No. 6,442,410) discloses a method for determining the blood glucose level based on an ocular refractive correction by measuring and then determining the ocular refractive correction to a database of known ocular refractive corrections and blood glucose concentrations.

The Chou patent (U.S. Pat. No. 6,477,393) discloses a technique and method for non-invasive blood glucose testing that includes irradiating a surface of a subject with a ring of electromagnetic radiation and detecting a portion of the displaced radiation by a CCD camera that generates detection signals for analysis by a processor resulting in a measurement of blood glucose concentration.

The Say et al. patent (U.S. Pat. No. 6,565,509) discloses a monitoring device and method that includes a transcutaneous electromechanical sensor responsive to an analyte enzyme and a sensor control unit for placement on skin that intermittently transmits data from analyte-dependent signals produced by the electromechanical sensor.

The Abbink et al. patent (U.S. Pat. No. 6,574,490) discloses an apparatus and method for non-invasive glucose measurement that includes a tissue sampling subsystem coupled to an illumination subsystem, a calibration maintenance subsystem, an FTIR spectrometer subsystem, and data acquisition subsystem and a computing subsystem for receiving a digital representation from the data acquisition subsystem and determining glucose concentrations from that digital representation.

In addition, a number of other minimumally invasive techniques exist or are being currently developed. For example, one method currently being investigated is a technique know as reverse iontophoresis in which fluid is extracted from the skin through the application of an electric current. Another technique involves transcutaneous harvesting of interstitial fluid from the skin using ultra fine needles, micro-laser drilling, ultrasonic, and disruption by chemicals. Also being developed is the use of a patch-like three-electrode system of glucose oxidase based sensors for measuring glucose transport across ultrasound treated skin. In addition, noninvasive optical techniques for glucose sensing and measuring include polarimetry, near-infrared optical absorption spectroscopy, far-infrared optical absorption spectroscopy, and Raman spectroscopy.

SUMMARY OF THE INVENTION

The present invention comprehends a non-invasive continuous blood glucose monitoring system and method that is a safe and portable system allowing diabetic patients to avoid the repeated needle sticks that are required for monitoring blood glucose levels. Using a real-time microprocessor controlled electronic feedback loop for glucose monitoring will make management of blood glucose automatic and continuous, and thus for the diabetic will reduce the cost and number of complications that occur because of inadequate management and control of the diabetes. As part of the present invention, a differential measurement system will include the use of two platinum wires or two thermistors calibrated to record temperatures with an accuracy of at least +/−0.035° Kelvin (K). The system and method of the present invention can continuously monitor the user's glucose level by making up to four measurements per minute since these devices stabilize in approximately 15 seconds. Two regions of the patient's ear will be used to measure temperature differentials to determine if the patient's blood glucose levels are rising or falling.

It is an objective of the present invention to provide a non-invasive blood glucose monitoring system that is painless, cost effective, practical and safe for continuous glucose monitoring.

It is another objective of the present invention to provide a non-invasive blood glucose monitoring system that uses two regions of the human ear to determine an increase or decrease in blood glucose levels.

It is yet another objective of the present invention to provide a non-invasive blood glucose monitoring system that is at least as accurate as the conventional finger stick method.

It is still another objective of the present invention to provide a non-invasive blood glucose monitoring system that substantially reduces temperature measurement errors by measuring the temperature of the anthelix and tragus of the diabetic patient's ear.

It is still yet another objective of the present invention to provide a non-invasive blood glucose monitoring system that combines the measured fasting blood glucose and HbA1c levels to determine a base line glucose reference level.

Yet still another objective of the present invention is to provide a non-invasive blood glucose monitoring system wherein either one or two sensors can be used to take two temperature measurements from separate regions of the ear after the base line glucose reference level has been determined in order to determine if blood glucose is increasing or decreasing.

Yet still a further objective of the present invention is to provide a non-invasive blood glucose monitoring system that provides accurate and continuous trending information to the patient by having the sensors in constant contact with the selected regions of the ear for temperature monitoring.

These and other objects, features and advantages will become apparent to one skilled in the art upon a perusal of the following detailed description when read in conjunction with the following drawings and appended claims.

DETAILED DESCRIPTION OF THE PREFERRED EMBODIMENT

Figure 1:
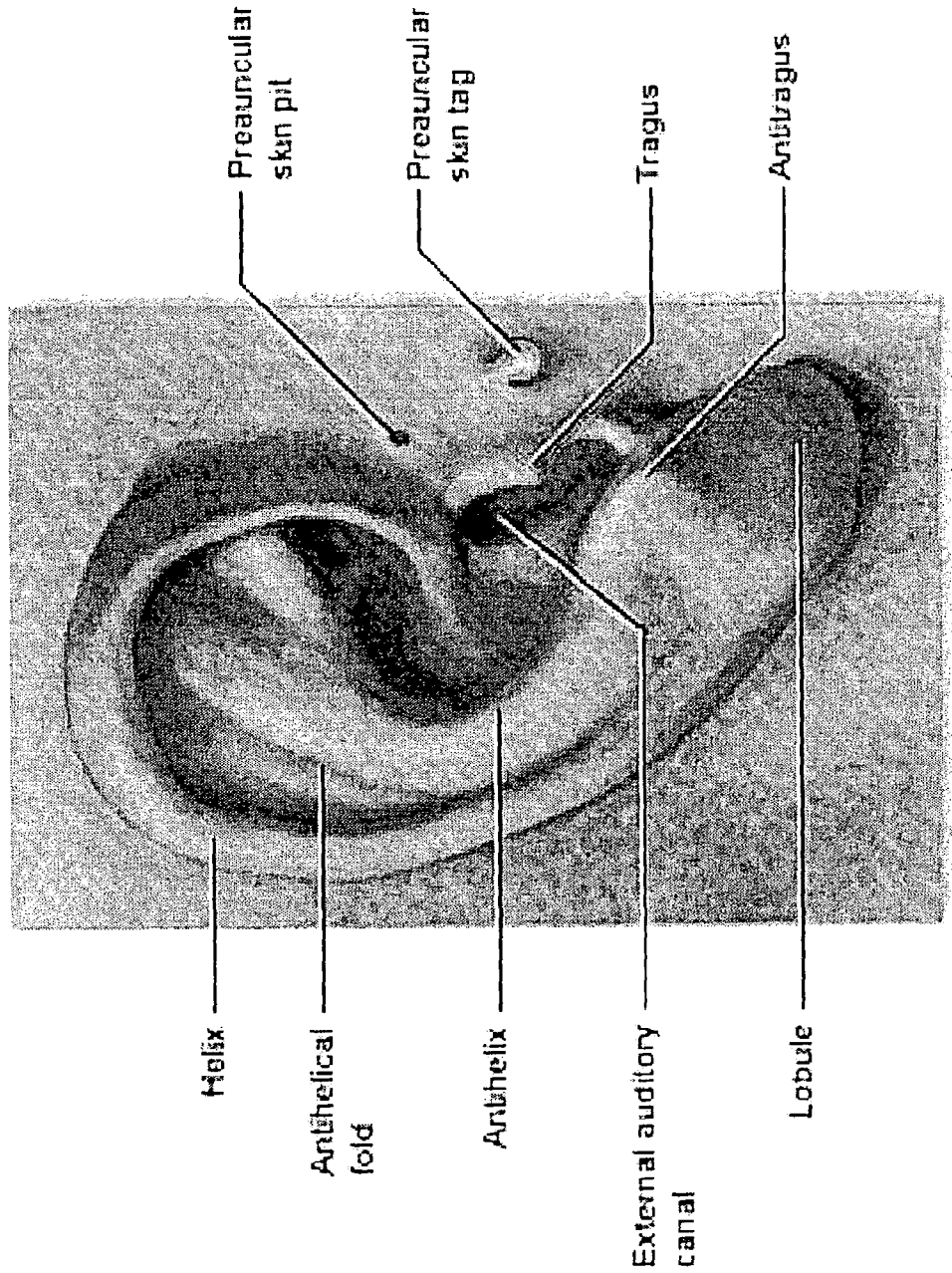
FIG. 1 is a drawing of an ear showing its constituent parts, including the anthelix and tragus.

FIG. 1 is an illustration of an ear showing the anthelix and tragus regions where the temperatures are taken in accordance with the present invention. In general, for diabetics to assess glucose metabolism testing can be done after a 12 hour fasting period to determine the fasting blood glucose level; with the normal range being 80–120 mg/dl. This allows the diabetic to determine the effectiveness of his or her control and management of blood glucose levels. In addition to the fasting blood glucose level, a second well-known reference value can be obtained by determining the HbA1c value, which is the test for glycosylated hemoglobin developed in the late 1970's. While fasting blood glucose level provides a snapshot of the glucose level at the time of testing, HbA1c testing reflects average glucose levels for the previous two to three months. Normally the same blood sample is used for testing fasting blood glucose and for testing the HbA1c level. Diabetics generally undergo this type of testing every six months as a recalibration to provide their medical team with the information necessary to manage their diabetes. The above tests for fasting blood glucose and HbA1c are done separately, though from the same blood sample, and a report is generally provided with two separate results: one number represents the fasting blood glucose level and one number represents the Hb1Ac level. The HbA1c is usually reported as a percentage and different people have different scales. While conversion factors vary, the present system and method uses a conversion factor chart to convert the HbA1c percentage to mg/dl. A conversion factor of 18.1 converts millimoles to mg/dl. The present invention will not create the need for additional tests, but uses the currently-obtained test data in a different way to enhance the individual's ability to manage his or her diabetes.

For obtaining a reference value, a key feature of the present system and method is to take the product of the values of a patient's fasting blood glucose and HbA1c, and then the square root of that product to provide a base line glucose reference level expressed in mg/dl. More specifically, the above-described square root of the product of the fasting blood glucose level and the HbA1c level becomes the base line glucose reference level that will be compared to temperature differences taken from locations on the patient's ear as hereinafter described. As will be described herein, this base line glucose reference level will be correlated with the person's temperature. Since there is a direct relationship between temperature and glucose level, subsequent temperature measurements of the person can be used to track increase or decrease in glucose level.

The system and method of the present invention requires at least one sensor—and preferably two sensors—that are capable of measuring temperature to at least an accuracy of ±0.035° K. The system and method is flexible in that the patient can use two sensors to take one measurement each or one sensor to take two different measurements. In the preferred embodiment, a device with two sensors will be configured so that each sensor will contact a preferred location on the patient's ear, specifically one sensor contacting the anthelix and one sensor contacting the tragus. See FIG. 1. Preferably the sensors can be two thermistors or two platinum wires that measure temperatures accurately to ±0.025 K and ±0.010 K respectively at 0.025 K and 0.010 K and one sensor would thus measure the temperature of the anthelix and one sensor would measure the temperature of the tragus. The applicant has found that 10 Kilo0ohm @ 25 C thermistors from Radio Shack or PT103 platinum wires from Lakeshore work well as sensors for the invention. The sensors actually provide a resistance that varies by temperature, allowing a resistance measurement that is then converted to a temperature at a high level of accuracy. In the preferred embodiment this resistance measurement would be read out in ohms, temperature and then in mg/dl as the final output.

The ear temperature measurements are done initially at the same time the person is undergoing the blood sample testing necessary to establish the person's base line glucose reference level, as described above. The temperature differential between the anthelix and tragus measurements taken at the same time as the testing for the base line glucose reference level establishes the base line temperature differential. This provides a fixed point correlating glucose level and temperature differential from which future measurements can be made. By way of example, if the person has a base line glucose reference level of 140 mg/dl and a base line temperature differential of 2.25° C., then by mathematical algorithm the instant glucose level at a future time can be calculated once the instant temperature differential is determined.

The present invention treats the above as a closed loop system wherein one gram of glucose yields 15.6 joules of energy. Further, it was determined that by calculating the ear mass and the specific heat transfer using the standard equation Q=MCPΔT that a temperature differential of approximately 0.024 K is equivalent to a change of 1 mg/dl. This conversion factor may change slightly for different individuals. The above numbers are applicable to the temperature differential of the specific locations of the ear, anthelix and tragus, as the temperature differential on other body parts is smaller and harder to measure. Thus, through the above calculations and measurements a number is obtained that relates temperature change to a change in blood glucose. In order to find any other blood glucose level, an instant temperature differential is taken and then compared to the reference temperature differential. Referring back to the example, previously given one can start with a base line temperature differential value of 2.25 at a baseline glucose reference level of 140 mg/dl, and, for example, posit an instant temperature differential of, say, 2 which is a lower temperature differential than the baseline value of 2.25. The present system and method has determined that a lower temperature differential corresponds to a higher blood glucose level and a higher temperature differential corresponds to a lower blood glucose level.

Continuing with the example, the difference between 2 and 2.25 is taken and then divided by the conversion number of 0.024 to arrive at the value of approximately 10. In the example this would thus be added to the person's base line glucose reference level (because the temperature differential has decreased), putting the patient's instant blood glucose level at 150 mg/dl. It should be noted that the settling time for sensors is 15 seconds and so up to four temperature differential readings per minute can be taken if two sensors are used, resulting in essentially continuous monitoring. It is known that the maximum blood glucose change is 4 mg/dl/minute. Thus multiple measurements per minute can be averaged to improve accuracy of glucose measurement.

Figure 2:
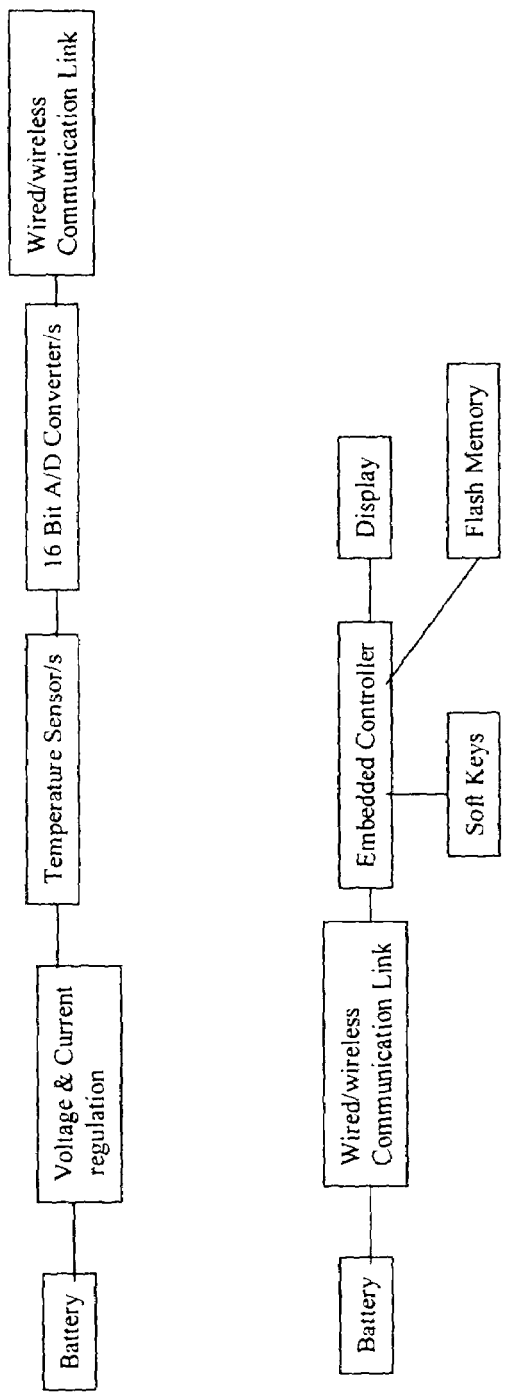
FIG. 2 is a block diagram of a typical system of the invention.

The system and method of the present invention is designed to provide accurate trending information regarding blood glucose levels so as to allow the diabetic to manage his or her condition. Thus, the physical units that comprise the invention will include the ability at the sensors to be worn at all times by mounting to the ear so that temperature differential can be continuously monitored. An analog reading will be taken from the temperature that will be converted to digital by an A/D converter. The converter output can be wireless sent to a receiver the user will carry in his or her pocket, for example, for receiving the output and translating the output into a digital readout. The communication from the sensors to the receiver can be either by wire or wireless means. The receiver will be able to store the raw numbers in memory. A microprocessor will also be part of the device and the microprocessor will compute instant blood glucose levels and the readings will be displayed along with date and time. The microprocessor will also have an application specific integrated circuit that will contain the algorithm necessary to make the glucose level calculations. It will include flash memory to store data and infrared or wireless data transmission to a personal computer or hand held device. For example, the microprocessor will be able to provide 14 day and 30 day averages. Thus, a printout could be obtained and provided to the patient's doctor that would contain for example the blood glucose levels, date and time for the previous month. This method provides more frequent measurement to improve accuracy compared to the accuracy of strips that are used in conjunction with the finger stick method. Shown in FIG. 2 is a block diagram showing a typical system using the present invention.

Although the system of the present invention has been described in a particular embodiment, it should be apparent to those skilled in the act that various alternative embodiments would be possible within the spirit and scope of the disclosure herein.

I claim:

1. A non-invasive blood glucose monitoring process, comprising:
   mounting one sensor adjacent to the tragus region of the ear of a human diabetic patient and one sensor adjacent to the anthelix region of the ear of a human diabetic:
   obtaining a value of a fasting blood glucose measurement;
   obtaining a value of an HbA1c measurement;
   multiplying the value of the fasting blood glucose by the value of the HbA1c measurement to get a product;
   taking the square root obtained from the product of the fasting blood glucose multiplied by the HbA1c and using this value as the base line glucose reference level;
   measuring the temperature of the tragus region of the ear using the adjacent sensor;
   measuring the temperature of the anthelix region of the ear using the adjacent sensor;
   determining the temperature differential between the tragus and anthelix with respect to the base line glucose reference glucose so that if the temperature differential subsequently decreases then the person's blood glucose has increased by 1 mg/dl per approximately 0.024° C. and if the temperature differential subsequently increases then the person's blood glucose has decreased by 1 mg/dl per approximately 0.024° C.

2. The process of claim 1 wherein the sensors are accurate to ±0.035 K.

3. The process of claim 2 wherein sampling the temperature of the anthelix region and the tragus region of the ear is done multiple times per minute by the adjacent sensor, resulting in essentially continuous monitoring.

4. The process of claim 3 wherein the temperature data is transmitted to an adjacently mounted microprocessor for analysis and readable output so that the diabetic patient can continuously monitor blood glucose levels.

5. A process for measuring the blood glucose level in a person by using differential ear temperatures, comprising the steps of:
   (a.) establishing a base line glucose reference level by
      (i.) testing a blood sample from the person taken after fasting to determine the fasting glucose level;
      (ii.) testing the same blood sample to determine the HbA1c level, as a percentage, and converting it to the same unit of measurement as the fasting glucose level;
      (iii.) multiplying the fasting glucose level by the HbA1c level to obtain a product;
      (iv.) taking the square root of the said product to determine a base line glucose reference level for the person;

(b.) establishing a base line temperature differential for the person, at substantially the same time as the blood sample from the previous step has been drawn, by:
  (i.) applying an external sensor at the tragus of the person's ear and obtaining a temperature measurement;
  (ii.) applying an external sensor at the anthelix of the person's ear and obtaining a temperature measurement;
  (iii.) calculating the temperature differential between the tragus temperature and the anthelix temperature to obtain a base line temperature differential;
(c.) at subsequent times, measuring the instant temperature differential at the tragus and anthelix of the person's ear by sensors in the same manner as set forth in step (b) above;
(d.) calculating the difference between the instant temperature differential and the base line temperature differential and dividing the result by a predetermined conversion factor to arrive at a glucose change amount;
(e.) adding the glucose change amount to the base line glucose reference level if the instant temperature differential is less than the base line temperature differential, or subtracting the glucose change amount from the base line glucose reference level if the instant temperature differential is greater than the base line temperature differential, to obtain the instant blood glucose level.

6. The process of claim 5 wherein the conversion factor is approximately 0.024.

7. The process of claim 6 wherein two external sensors are used, one applied to the tragus and one applied to the anthelix so that the respective temperature measurements can be simultaneously.

8. The process of claim 7 wherein the sensors are accurate to ±0.035 K.

9. The process of claim 8 wherein the sensors are either thermistors or platinum wires.

10. The process of claim 9 wherein the temperature measurements are taken multiple times per minute resulting in essentially continuous monitoring.

11. The process of claim 10 wherein the instant temperature differential and instant blood glucose level is transmitted to, via wire or wirelessly, and stored within a microprocessor and made available for display and averaging or other manipulation.

\* \* \* \* \*